US006267948B1

(12) United States Patent
Ren et al.

(10) Patent No.: US 6,267,948 B1
(45) Date of Patent: *Jul. 31, 2001

(54) DERMATOLOGICAL FORMULATIONS AND METHODS

(75) Inventors: Wu Yun Ren, Germantown, MD (US); Michael Seidman, Washington, DC (US); David A. Brown, Ellicott City, MD (US)

(73) Assignee: Applied Genetics Incorporated Dermatics, Freeport, NY (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/055,274

(22) Filed: Apr. 6, 1998

(51) Int. Cl.$^7$ ............... A61K 7/42; A61K 7/06; A61K 31/19; A61K 31/045; A61K 31/07

(52) U.S. Cl. ............ 424/59; 424/70.1; 424/70.6; 424/70.9; 424/401; 514/557; 514/724; 514/725; 514/728

(58) Field of Search ............... 424/59, 401, 70.1, 424/70.6, 70.9; 514/557, 724, 725, 728

(56) References Cited

U.S. PATENT DOCUMENTS

| 5,130,136 | | 7/1992 | Shono et al. . | |
|---|---|---|---|---|
| 5,352,440 | | 10/1994 | Gilchrest et al. | 424/59 |
| 5,470,579 | * | 11/1995 | Bonte et al. | 424/450 |
| 5,532,001 | | 7/1996 | Gilchrest et al. | 424/450 |
| 5,554,359 | | 9/1996 | Fuller | 424/59 |
| 5,698,184 | * | 12/1997 | Pickart | 424/59 |
| 5,700,450 | | 12/1997 | Gilchrest et al. . | |
| 5,744,128 | * | 4/1998 | Holick | 424/60 |
| 5,942,531 | * | 8/1999 | Diaz et al. | 514/394 |
| 5,990,177 | * | 11/1999 | Brown | 514/729 |

FOREIGN PATENT DOCUMENTS

WO 98/11882    3/1998  (WO) .

OTHER PUBLICATIONS

Van Scott et al, "Control of Keratinization with α–Hydroxy Acids and Related Compounds", Arch Dermatol., 110:586–590, 1974.
Van Scott et al, "Hyperkeratinization, corneocyte cohesion, and alpha hydroxy acids", J. Amer. Acad. of Dermatol., 11(5):867–879, 1984.
Van Scott et al, "Alpha Hydroxy Acids: Procedures for Use in Clinical Practice", Cutis, 43:222–228, 1989.
Ridge et al, "Use of α–hydroxy acids in the therapy for 'photoaged' skin", J. of Amer. Acad. of Dermatol., 23(5):932, 1990.
Moy et al, "Glycolic Acid Therapy: Evaluation of Efficacy and Techniques in Treatment of Photodamage Lesions", The Amer. J. Cosmetic Surgery, 10(1):9–13, 1993.
Perricone et al, "Photoprotective and Antiinflammatory Effects of Topical Glycolic Acid", Amer. Soc. for Dermatol. Surgery, 22:435–437, 1996.
Ditre et al, "Effects of α–hydroxy acids on photoaged skin: A pilot clinical, histologic, and ultrastructural study", J. of Amer. Acad. Dermatol., 34(2):187–195, 1996.
Stiller et al, "Topical 8% Glycolic Acid and 8% L–Lactic Acid Creams for the Treatment of Photodamaged Skin", Arch Dermatol., 132:631–636, 1996.
Piacquadio et al, "Short Contact 70% Glycolic Acid Peels as a Treatment for Photodamaged Skin", Amer. Soc. for Dermatol. Surgery, 22:449–452, 1996.
B.A. Gilchrest, "A review of skin ageing and it medical therapy", British J. of Dermatologists, 135:867–875, 1996.
Bernstein et al, "Citric Acid Increases Viable Epidermal Thickness and Glycosaminoglycan Content of Sun–damaged Skin", Amer. Soc. for Dermatol. Surgery, 23:689–694, 1997.
Fuller et al, "Hormonal Regulation of Melanogenesis in Mouse Melanoma and in Human Melanocytes", Ann. NY Acad. Sci., 680:302–319, 1993.
Allan et al, "Topically Applied Diacylglycerols Increase Pigmentation in Guinea Pig Skin", J. of Investigative Dermatol., 105(5):687–692, 1995.
"DNA damage and melanogenesis", Nature, 372:413, 1994.
Jimbow et al, "Biochemistry and Physiology of Melanin Pigmentation", Physiol., Biochem., and Molecular. Biol. of the Skin, 2$^{nd}$ Edition, 873–908, 1991.
Jimbow et al, "Biology of Melanocytes", Fourth Ed. Dermatol. in Gen. Med., 1:261–289.
Gilchrest et al, "Mechanisms of Ultraviolet Light–Induced Pigmentation", Photochemistry and Photobiology, 63(1):1–10, 1996.
Barthelman, et al., "Inhibitory Effects of Perillyl Alcohol on UVB–induced Murine Skin Cancer and AP–1 Transactivation," Cancer Research, 1998, 58:711–716.
Brown et al., "Aliphatic and Alicyclic Diols Induce Melanogenesis in Cultured Cells and Guinea Pig Skin," Journal of Investigative Dermatology, 1998, 110:428–437.
Kitahara et al., "Evaluation of Skin Damage of Cyclic Monoterpenes, Percutaneous, Absorption Enhancers, by Using Cultured Human Skin Cells," Biol. Pharm. Bull., 1993, 16;912–916.

* cited by examiner

Primary Examiner—Shelley A. Dodson
Assistant Examiner—Marina Lamm
(74) Attorney, Agent, or Firm—Maurice M. Klee

(57) ABSTRACT

A method and dermatological formulation are provided for increasing the pigmentation response of mammalian skin, hair, wool or fur to agents which stimulate melanogenesis. The method comprises administering to mammalian skin, hair, wool or fur a dermatological formulation containing a melanogenesis-stimulating effective amount of an agent which stimulates melanogenesis in melanocytes, and a melanogenesis-enhancing effective amount of an agent, such as an α-hydroxy acid, which enhances the stimulation of melanogenesis by the melanogenesis-stimulation agent.

13 Claims, 1 Drawing Sheet

DERMATOLOGICAL FORMULATIONS AND METHODS

BACKGROUND OF THE INVENTION

1. Field of the Invention

The present invention relates to enhancing the pigmentation response to inducers of melanogenesis by inclusion of melanogenesis-enhancing agents in formulations applied to skin, hair, wool or fur.

2. Description of the Related Art

There have been various descriptions of the use of compounds for stimulating melanogenesis or pigmentation. U.S. Pat. No. 5,352,440 describes increasing melanin synthesis in melanocytes and increasing pigmentation by administration of certain diacylglycerol compounds. Increased pigmentation in mammalian skin via administration of certain DNA fragments is disclosed in U.S. Pat. No. 5,532,001. U.S. Pat. No. 5,554,359 is directed to increasing levels of melanin in melanocytes by administration of lysosomotropic agents. And various melanogenic diols are described in Brown et al., 1998, J. Invest. Dermatol., 110:428–427.

While certain methods and compositions for stimulating pigmentation are known, there exists a need for improvements in the art. The present invention provides improved methods and compositions for stimulating pigmentation responses in mammalian skin, hair, wool or fur.

SUMMARY OF THE INVENTION

The present invention provides a method for increasing the pigmentation response of mammalian skin, hair, wool or fur to agents which stimulate melanogenesis, comprising administering to mammalian skin, hair, wool or fur a dermatological formulation comprising a melanogenesis-stimulating effective amount of an agent which stimulates melanogenesis in melanocytes, and a melanogenesis-enhancing effective amount of an agent which enhances the stimulation of melanogenesis by the melanogenesis-stimulating agent. More particularly, the melanogenesis-enhancing compounds are selected from among α-hydroxy acids, salts and derivatives thereof; α-keto acids, salts and derivatives thereof; β-hydroxy acids, salts and derivatives thereof; retinoids, salts and derivatives thereof; Vitamin A and related compounds; acids such as trichloroacetic acid and trifluoroacetic acid; phenol; and, methoxypropyl-gluconamide.

Another aspect of the present invention provides a dermatological formulation for increasing the pigmentation response of mammalian skin, hair, wool or fur to agents which stimulate melanogenesis. The formulation comprises a melanogenesis-stimulating effective amount of an agent which stimulates melanogenesis in melanocytes, and a melanogenesis-enhancing effective amount of an agent which enhances the stimulation of melanogenesis by the melanogenesis-stimulating agent. More particularly, the melanogenesis-enhancing compounds are selected from among α-hydroxy acids, salts and derivatives thereof; α-keto acids, salts and derivatives thereof; β-hydroxy acids, salts and derivatives thereof; retinoids, salts and derivatives thereof; Vitamin A and related compounds; acids such as trichloroacetic acid and trifluoroacetic acid; phenol; and, methoxypropyl-gluconamide.

DESCRIPTION OF THE PREFERRED EMBODIMENTS

Figure 1:
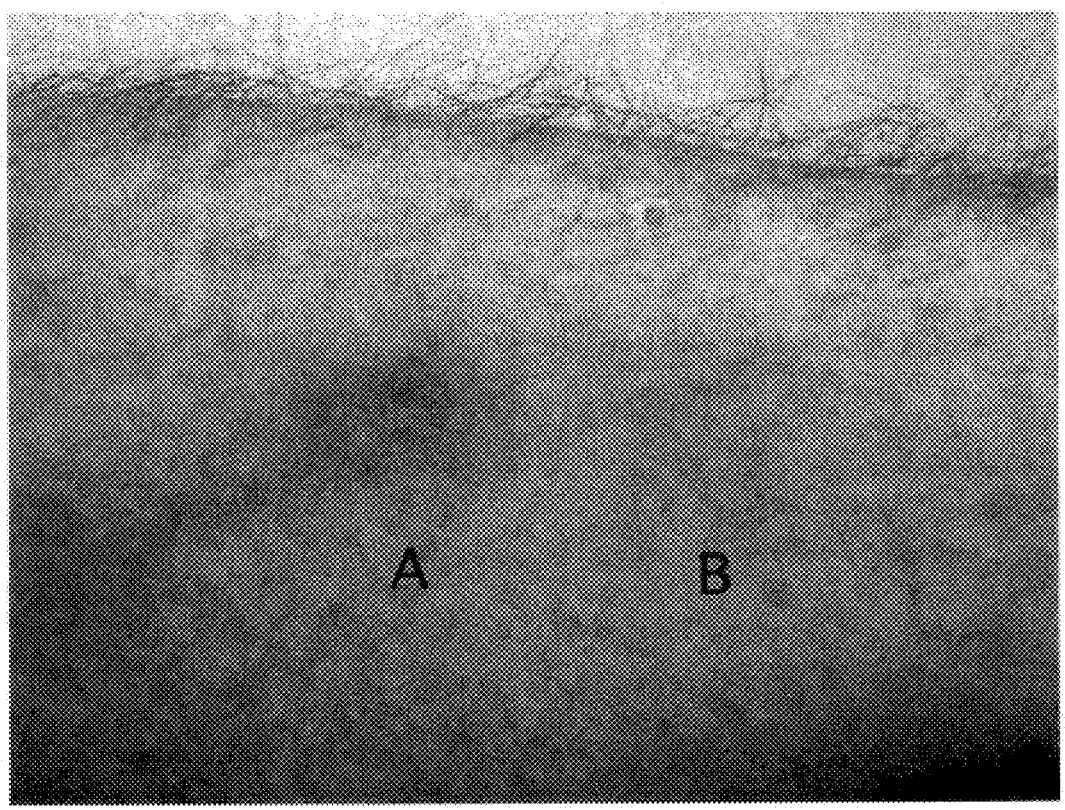
FIGS. 1A–1B illustrate skin pigmentation responses.

This invention is based on the unique observation that certain compounds greatly increase the pigmentation response in mammalian skin treated with agents known to stimulate melanin production in melanocytes. Thus, the present invention is useful in the treatment of hypopigmentation disorders, such as albinism, vitiligo, etc. It is also believed that increasing the pigmentation of skin according to the present invention will protect such skin from subsequent UV light damage, sunburn, photoaging and development of skin cancers.

The present invention may be used in the treatment of any mammalian skin, hair, wool or fur. Treatment of human skin is preferred.

As discussed above, the present invention provides for an increased pigmentation response by administration of a composition comprising (1) an agent which stimulates melanin production in melanocytes (i.e., a melanogenesis-stimulating agent), and (2) a compound which enhances pigmentation by the melanogenesis-stimulating agent (i.e., a melanogenesis-enhancing agent). The melanogenesis-enhancing agent serves to provide a greater pigmentation response to a melanogenesis-stimulating agent than would otherwise occur.

Melanogenesis-stimulating agents according to the present invention include melanogenic diols, triols and alcohols including but not limited to derivatives of norbornane, pinane and camphane; 3-isobutyl-1-methylxanthine 1,3-disubstituted xanthine, theophylline and its analogs and derivatives; diacylglycerol and its analogs including but not limited to 1-oleoyl-2-acetyl-glycerol, 1-oleoyl-2-butanoyl-glycerol, 1,2-diacetyl-glycerol, 1,2-butanoyl-glycerol, and 1-hexanoyl-2-oleoyl-glycerol; lysosomotropic agents; and DNA fragments. Any melanogenesis-stimulating agent may be used as long as its ability to stimulate melanogenesis is increased by the melanogenesis-enhancing agent.

Preferred melanogenesis-stimulating agents are the melanogenic diols, triols and alcohols as described in U.S. Application Ser. No. 08/933,143, filed Sep. 18, 1997, now abanded PCT/US98/05346 entitled "Pharmaceutical Compositions and Methods", filed Mar. 18, 1998, which was published as WO 98/55085 Dec. 10, 1988, the which was published as WO 98/55085 on Dec. 10, 1999, contents of which are hereby incorporated by reference. Especially preferred melanogenic diols, triols and alcohols for use according to the present invention include 2,3-cis/exo-pinanediol ([1R,2R,3S,5R]-[−]-pinanediol and [1S,2S,3R,5S]-[+]-pinanediol); 2,3-cis/exo-bornanediol; 5-norbornene-2,2-dimethanol; norbornene-2,2-dimethanol; 2-hydroxy-2-norbornanemethanol; 1-(exo-2-norbornyl-)-propan-1,2-diol; and, 1-(endo-2-norbornyl-)-propan-1,2-diol.

Melanogenesis-enhancing agents according to the present invention include α-hydroxy acids, salts and derivatives thereof such as glycolic acid, lactic acid, ammonium lactate, mandelic acid, benzilic acid, malic acid, tartaric acid, gluconic acid and citric acid; α-keto acids, salts and derivatives thereof such as pyruvic acid; β-hydroxy acids, salts and derivatives thereof such as salicylic acid; retinoids, salts and derivatives thereof such as tretinoin and isotretoin; Vitamin A, Vitamin $A_2$ and Vitamin A aldehyde; acids such as trichloroacetic acid and trifluoroacetic acid; phenol; and, methoxypropyl-gluconamide. The aforementioned compounds possess properties such as the ability to diminish epidermal corneocyte cohesion, reduce stratum corneum thickness, stimulate keratinocyte proliferation, increase epidermal thickness, result in more even distribution of melanocytes, result in more even distribution of melanin, and to stimulate dispersal of melanin. Any melanogenesis-enhancing agent may be used as long as it enhances the ability of a melanogenesis-stimulating agent to increase melanin production by melanocytes. Alpha-hydroxy acids are the preferred melanogenesis-enhancing agent.

Alpha-hydroxy acids have not been reported to possess melanogenic ability. In fact, α-hydroxy acids have been used to reduce hyperpigmentation of photoaged skin (Van Scott, E. J., and Yu, R. J., 1989, Cutis 43:222–228; Stiller et al., 1996, Arch. Dermatol. 132:631–636). The present inventors, however, suggest that the effects of α-hydroxy acids which reduce pigmentation of photoaged skin are likely to be the same effects which increase the pigmentation response to agents that stimulate melanogenesis in melanocytes. Specifically, α-hydroxy acids have been reported to result in "more even distribution of melanocytes and melanin pigment"(Gilchrest, B. A., 1996, Br. J. Dermatol. 135:867–875), "less clumping of melanin pigmentation with α-hydroxy acid treatment" and "dispersal of melanin pigmentation" (Ditre, C. M. et al., 1996, J. Am. Acad. Dermatol. 34:187–195). In addition, α-hydroxy acid treatment results in increased proliferation and turnover of keratinocytes, which increases the rate of transport of melanin to the surface layers of the skin where it is sloughed off. In the absence of stimulation of melanogenic activity, the net result is an accelerated rate of loss of pigmentation. However, by the present invention it is contemplated that when α-hydroxy acids, or melanogenesis-enhancing agents in general, are applied to skin with a melanogenesis-stimulating agent, the α-hydroxy acids (or melanogenesis-enhancing agents) assist the processes of melanogenesis by enhancing distribution of melanin through the epidermis.

The natural tanning response as elicited by solar irradiation stimulates not only melanin production in melanocytes, but also proliferation of keratinocytes such that transport of melanin through the epidermis is enhanced (Jimbow, K., et al., 1991. Biochemistry and physiology of melanin production, pages 873–909, In: Physiology, Biochemistry, and Molecular Biology of the Skin, L. A. Goldsmith, ed. Oxford University Press, New York, USA.; Jimbow, K., et al., 1993. Biology of melanocytes, pages 261–289, In: Dermatology in General Medicine, Volume 1, Fourth Edition, T. B. Fitzpatrick et al., ed. McGraw-Hill, Inc., New York). Melanogenic diols act directly on melanocytes to stimulate melanogenesis (Brown et al., 1997, J. Invest. Dermatol., In Press), but there is no evidence to indicate that melanogenic diols stimulate proliferation of human keratinocytes. Thus, they may stimulate only part of the physiological response necessary for effective tanning.

It is contemplated that melanogenesis-enhancing agents, e.g., α-hydroxy acids, complete the requirements for effective tanning by stimulating the proliferation of keratinocytes and thereby facilitating the distribution of melanin throughout the epidermis. Furthermore, the reduced clumping of melanin and increased dispersal of melanin which are enhanced by α-hydroxy acids are well-known features of darkly pigmented skin (Jimbow, K., et al., 1993. Biology of melanocytes, pages 261–289, In: Dermatology in General Medicine, Volume 1, Fourth Edition, T. B. Fitzpatrick et al., ed. McGraw-Hill, Inc., New York).

It is further contemplated that all agents which are presently used for repair of photoaging and/or stimulation of epidermal turnover (skin refreshing or peeling) will be effective as melanogenesis-enhancing agents in facilitating the pigmentation response induced by melanogenesis-stimulating agents.

The methods and compositions of the present invention contemplate the use of one or more melanogenesis-stimulating agents as an active ingredient to stimulate melanogenesis, and one or more melanogenesis-enhancing agents to enhance pigmentation. In a preferred embodiment, the active ingredients are combined with an acceptable carrier to form a topical formulation which may be placed on the skin. Topical formulations may include ointments, lotions, pastes, creams, gels, drops, suppositories, sprays, liquids, shampoos, powders and transdermal patches. Thickeners, diluents, emulsifiers, dispersing aids or binders may be used as needed. Preferably, one function of the carrier is to enhance skin penetration of the active ingredients, and should be capable of delivering the active ingredients to melanocytes under in vivo conditions. Suitable carriers are well known to one of ordinary skill, and include liposomes, ethanol, dimethylsulfoxide (DMSO), petroleum jelly (petrolatum), mineral oil (liquid petrolatum), water, dimethylformamide, dekaoxyethylene-oleylether, oleic acid, 2-pyrrolidone and Azone® brand penetration enhancer (Upjohn). Depending on the specific application, the compositions of the present invention may also include other active ingredients, as well as inert or inactive ingredients.

The dose regimen will depend on a number of factors which may readily be determined, such as severity and responsiveness of the condition to be treated, but will normally be one or more doses per day, with a course of treatment lasting from several days to several months, or until a cure is effected or a diminution of disease state is achieved, or a cosmetically desired degree of melanogenesis (tanning) is achieved, depending on the application. One of ordinary skill may readily determine optimum dosages, dosing methodologies and repetition rates. In general, it is contemplated that topical formulations (such as creams, lotions, solutions, etc.) will have a concentration of melanogenesis-stimulating agent of from about 0.01% to about 50%, preferably from about 0.1% to about 10%.

It is contemplated that melanogenesis-enhancing agents will be used at concentrations which diminish epidermal corneocyte cohesion, reduce stratum corneum thickness, stimulate keratinocyte proliferation, and increase epidermal thickness, without resulting in the phenomena known as "chemical peeling" (Piacquadio, D., et al., 1996, Dermatol. Surg. 22:449–452). As such, the effective concentrations of melanogenesis-enhancing agents are expected to be in the range of 5% to 25% by weight (Stiller et al., 1996, Arch. Dermatol. 132:631–636; Ditre et al., 1996, J. Am. Acad. Dermatol. 34:187–195). However, in some cases where reparation of photodamaged skin is desirable prior to induction of pigmentation (tanning), it is contemplated that much higher concentrations of melanogenesis-enhancing agents may be used. Additionally, it is contemplated that short-term higher concentrations of melanogenesis-enhancing agents may be used instead of longer term application of lower concentrations of melanogenesis-enhancing agents.

The use of and useful and novel features of the present methods and compositions will be further understood in view of the following non-limiting examples.

EXAMPLE 1

The melanogenic agent 2,3-R-pinanediol (2,3-R-PD) was formulated with inclusion of an α-hydroxy acid cream as follows:

|    | 70% Isopropyl Alcohol* | 2,3-R-Pinanediol | α-Hydroxy Acid Cream** | 1,2-Propylene Glycol |
|----|---|---|---|---|
| #1 | 165 µl | 85 mg | 250 µl |  |
| #2 |  | 85 mg | 250 µl | 165 µl |

*70% Isopropyl Rubbing Alcohol (CVS)
**Alpha Hydroxy Face Cream (CVS) which contains 8% active alpha hydroxy acids 10 µl of each solution was applied 3 times per day to the skin of a human subject. Solution #1 was applied for 6 days, while solution #2 was applied for 3 days. Solution #1 resulted in no irritation or erythema during the 6 day application period, while solution #2 resulted in irritation and erythema on the third day of application. Treated spots were subjectively evaluated for pigmentation response using a subjective rating system as follows: 0=no change from background; +0.25=slight darkening, indistinct; +0.5=slight darkening, distinct; +1=slight-moderate darkening; +2 moderate, even darkening; +3=substantial, even darkening; +4=profound, even darkening.

When evaluated for pigmentation response 5 days after the cessation of applications, the location where Solution #1 was applied (FIG. 1A) exhibited moderate even darkening (pigmentation rating=2), while the spot where Solution #2 was applied (FIG. IB) exhibited slight to moderate darkening (pigmentation rating=1). In a previous experiment in which 10 µl 2,3-R-pinanediol dissolved in 100% ethanol was applied to the same subject 3–8 times per day for 6 days, the maximum pigmentation response obtained was slight darkening (pigmentation rating=0.5). These findings show that inclusion of α-hydroxy acid in formulations results in 4-fold enhancement of the pigmentation response induced by 2,3-R-pinanediol.

Pigmentation of the location where Solution #1 was applied became apparent approximately 2 days after the final day of application. Pigmentation response where Solution #1 as applied exhibited the following temporal pattern of pigmentation:

| Days After Cessation of Solution #1 Application | Pigmentation Response* |
|---|---|
| 2 | 0.5 |
| 3 | 1 |
| 4 | 1.5 |
| 6 | 2.5 |
| 7 | 2 |
| 9 | 1.5 |
| 12 | 1 |
| 13 | 0.5 |
| 15 | 0.25 |

*Subjective rating scale where: 0 = no change from background; +0.25 = slight darkening, indistinct; +0.5 = slight darkening, distinct; +1 = slight-moderate darkening; +2 = moderate, even darkening; +3 = substantial, even darkening; +4 = profound, even darkening.

Alpha-hydroxy acids do not induce melanogenesis. however α-hydroxy acids are known to diminish epidermal corneocyte cohesion reduce, stratum corneum thickness, stimulate keratincyte proliferation, increase epidermal thickness, result in more even distribution of melanocytes, result in even distribution of melanin, and stimulate dispersal of malanin. Therefore, it is contemplated that α-hydroxy facilitate melanogenesis induced by 2,3-R-pinanediol by diminishing clumping of melanin, by stimulating dispersal of melanin including passage into keratinocytes, and by accelerating transport of melanin through the epidermis by stimulating proliferation of keratinocytes.

There are no reports of α-hydroxy face cream or ingredients therein stimulating melanogenesis. Thus, it contemplate that is the unique combination of agents which stimulate melanin production in melanocytes (e.g, melanogenic diols), and α-hydroxy acids which stimulate proliferation of keratinocytes with resultant melanin mobilization, that results in marked induction of skin pigmentation or sunless tanning. Further, it is contemplated that this combination of stimulation of melanin production in melanocytes, and stimulation of keratinocyte proliferation in epidermis, parallels the major physiological responses involved in the natural tanning process induced by solar irradiation.

We claim:

1. A method for increasing the pigmentation response of mammalian skin, hair, wool or fur to agents which stimulate melanogenesis, comprising administering to mammalian skin, hair, wool or fur a dermatological formulation comprising a melanogenesis-stimulating effective amount of an agent which stimulates melanogenesis in melanocytes, and a melanogenesis-enhancing effective amount of an agent which enhances the stimulation of melanogenesis by the melanogenesis-stimulating agent wherein:

(a) the agent which stimulates melanogenesis in melanocytes is a melanogenic diol selected from the group consisting of derivatives of norbornane, pinane, and camphane; and (b) the melanogenesis-enhancing agent is selected from the group consisting of α-hydroxy acids, salts and derivatives thereof; α-keto acids, salts and derivatives thereof; β-hydroxy acids, salts and derivatives thereof; retinoids, salts and derivatives thereof; Vitamin A and related compounds; trichloroacetic acid; trifluoroacetic acid; phenol; and, methoxypropyl-gluconamide.

2. The method according to claim 1, wherein the melanogenesis-enhancing agent comprises α-hydroxy acids.

3. The method according to claim 2, wherein the α-hydroxy acid is selected from the group consisting of glycolic acid, lactic acid, ammonium lactate, mandelic acid, benzilic acid, malic acid, tartaric acid, gluconic acid and citric acid.

4. The method according to claim 1, wherein the dermatological formulation is administered to human skin.

5. The method according to claim 1, wherein the melanogenesis-stimulation agent comprises 2,3-R-pinanediol.

6. A dermatological formulation for increasing the pigmentation response of mammalian skin, hair, wool or fur to agents which stimulate melanogenesis, comprising a melanogenesis-stimulating effective amount of an agent which stimulates melanogenesis in melanocytes, and a melanogenesis-enhancing effective amount of an agent which enhances the stimulation of melanogenesis by the melanogenesis-stimulating agent wherein:

(a) the agent which stimulates melanogenesis in melanocytes is a melanogenic diol selected from the group consisting of derivatives of norbornane, pinane, and camphane; and (b) the melanogenesis-enhancing agent is selected from the group consisting of α-hydroxy acids, salts and derivatives thereof; α-keto acids, salts and derivatives thereof; β-hydroxy acids, salts and derivatives thereof; retinoids, salts and derivatives thereof; Vitamin A and related compounds; trichloroacetic acid; trifluoroacetic acid; phenol; and, methoxypropyl-gluconamide.

7. The formulation according to claim 6, wherein the melanogenesis-enhancing agent comprises α-hydroxy acids.

8. The formulation according to claim 7, wherein the α-hydroxy acid is selected from the group consisting of glycolic acid, lactic acid, ammonium lactate, mandelic acid, benzilic acid, malic acid, tartaric acid, gluconic acid and citric acid.

9. The formulation according to claim 6, wherein the melanogenesis-stimulation agent comprises 2,3-R-pinanediol.

10. The method according to claim 1, wherein the agent which stimulates melanogenesis in melanocytes is selected from the group consisting of 2,3-cis/exo-pinanediol; 2,3-cis/exo-bornanediol; 5-norbornene-2,2-dimethanol; norbornane-2,2-dimethanol; 2-hydroxy-2-norbornanemethanol; 1-(exo-2-norbornyl-)-propan-1,2-diol; and 1-(endo-2- norbornyl-)-propan-1,2-diol.

11. The method according to claim 1, wherein the agent which stimulates melanogenesis in melanocytes is 2,3-cis/exo-pinanediol.

12. The formulation according to claim 6, wherein the agent which stimulates melanogenesis in melanocytes is selected from the group consisting of 2,3-cis/exo-pinanediol; 2,3-cis/exo-bornanediol; 5-norbornene-2,2-dimethanol; norbornane-2,2-dimethanol; 2-hydroxy-2-norbornanemethanol; 1-(exo-2-norbornyl-)-propan-1,2-diol; and 1-(endo-2-norbornyl-)-propan-1,2-diol.

13. The formulation according to claim 6, wherein the agent which stimulates melanogenesis in melanocytes is 2,3-cis/exo-pinanediol.

* * * * *